(12) United States Patent
Koike et al.

(10) Patent No.: US 10,352,842 B2
(45) Date of Patent: Jul. 16, 2019

(54) PARTICULATE MATTER DETECTION ELEMENT AND PARTICULATE MATTER DETECTION SENSOR

(71) Applicant: DENSO CORPORATION, Kariya, Aichi-pref. (JP)

(72) Inventors: Kazuhiko Koike, Nishio (JP); Hironobu Shimokawa, Nishio (JP); Masayuki Tamura, Kariya (JP); Go Miyagawa, Kariya (JP); Tomotaka Mouri, Kariya (JP)

(73) Assignee: DENSO CORPORATION, Kariya (JP)

( * ) Notice: Subject to any disclaimer, the term of this patent is extended or adjusted under 35 U.S.C. 154(b) by 74 days.

(21) Appl. No.: 15/524,738

(22) PCT Filed: Sep. 8, 2015

(86) PCT No.: PCT/JP2015/075432
§ 371 (c)(1),
(2) Date: May 5, 2017

(87) PCT Pub. No.: WO2016/072146
PCT Pub. Date: May 12, 2016

(65) Prior Publication Data
US 2017/0322134 A1    Nov. 9, 2017

(30) Foreign Application Priority Data
Nov. 6, 2014  (JP) .................... 2014-226161

(51) Int. Cl.
*G01N 15/06*  (2006.01)
*G01B 7/34*  (2006.01)
(Continued)

(52) U.S. Cl.
CPC .............. *G01N 15/06* (2013.01); *G01B 7/34* (2013.01); *G01M 15/102* (2013.01);
(Continued)

(58) Field of Classification Search
CPC .......... G01N 15/06; G01N 27/04; G01B 7/34; G01M 15/102
See application file for complete search history.

(56) References Cited

U.S. PATENT DOCUMENTS 5,458,664 A * 10/1995 Ishii .................. B01D 39/2051
55/282
5,664,986 A * 9/1997 Roh ...................... B24B 37/015
451/285
(Continued)

FOREIGN PATENT DOCUMENTS

| JP | 2011-080926 | 4/2011 |
|---|---|---|
| JP | 2012-078130 | 4/2012 |
| JP | 2012-220257 | 11/2012 |

OTHER PUBLICATIONS

International Search Report dated Nov. 17, 2015 issued in corresponding Application No. PCT/JP2015/075432 (2 pages).

*Primary Examiner* — Tung X Nguyen
*Assistant Examiner* — Dominic E Hawkins
(74) *Attorney, Agent, or Firm* — Nixon & Vanderhye P.C.

(57) ABSTRACT

A particulate matter detection element 1 includes paired detection electrodes 12 for detecting particulate matter contained in exhaust gas discharged from an internal combustion engine, and insulating member 13 made of electrically insulating material. In the particulate matter detection element 1, at least part of the paired detection electrodes 12 is exposed from the insulating member 13 in the direction perpendicular to the lamination direction of the paired detection electrodes 1, to cause part of the particulate matter to deposit thereon. The surface roughness of at least the insulating member disposed between the paired detection electrodes is between 0.8 μm and 8.0 μm in 10-point average roughness.

4 Claims, 6 Drawing Sheets

(51) Int. Cl.
  *G01M 15/10* (2006.01)
  *G01N 15/00* (2006.01)
  *G01N 27/04* (2006.01)

(52) U.S. Cl.
  CPC ..... *G01N 15/0606* (2013.01); *G01N 15/0656* (2013.01); *G01N 27/04* (2013.01); *G01N 2015/0046* (2013.01)

(56) References Cited

U.S. PATENT DOCUMENTS

| | | | |
|---|---|---|---|
| 2009/0309571 A1* | 12/2009 | Katsuyama | G01N 15/0656 324/71.1 |
| 2010/0147052 A1* | 6/2010 | Nelson | G01N 15/0656 73/28.01 |
| 2011/0107815 A1* | 5/2011 | Nelson | F02D 41/1466 73/23.33 |
| 2012/0110983 A1* | 5/2012 | Griffith | F01N 11/002 60/277 |
| 2013/0145815 A1* | 6/2013 | Nishijima | F02D 41/1446 73/1.06 |
| 2013/0283886 A1* | 10/2013 | Teranishi | G01N 33/0047 73/23.31 |
| 2014/0007650 A1* | 1/2014 | Mitani | B03C 3/41 73/23.31 |
| 2014/0342178 A1* | 11/2014 | Saito | C25D 1/04 428/606 |
| 2015/0331188 A1* | 11/2015 | Maeda | G02B 6/132 385/131 |
| 2016/0363522 A1* | 12/2016 | Chung | F01N 9/002 |

* cited by examiner

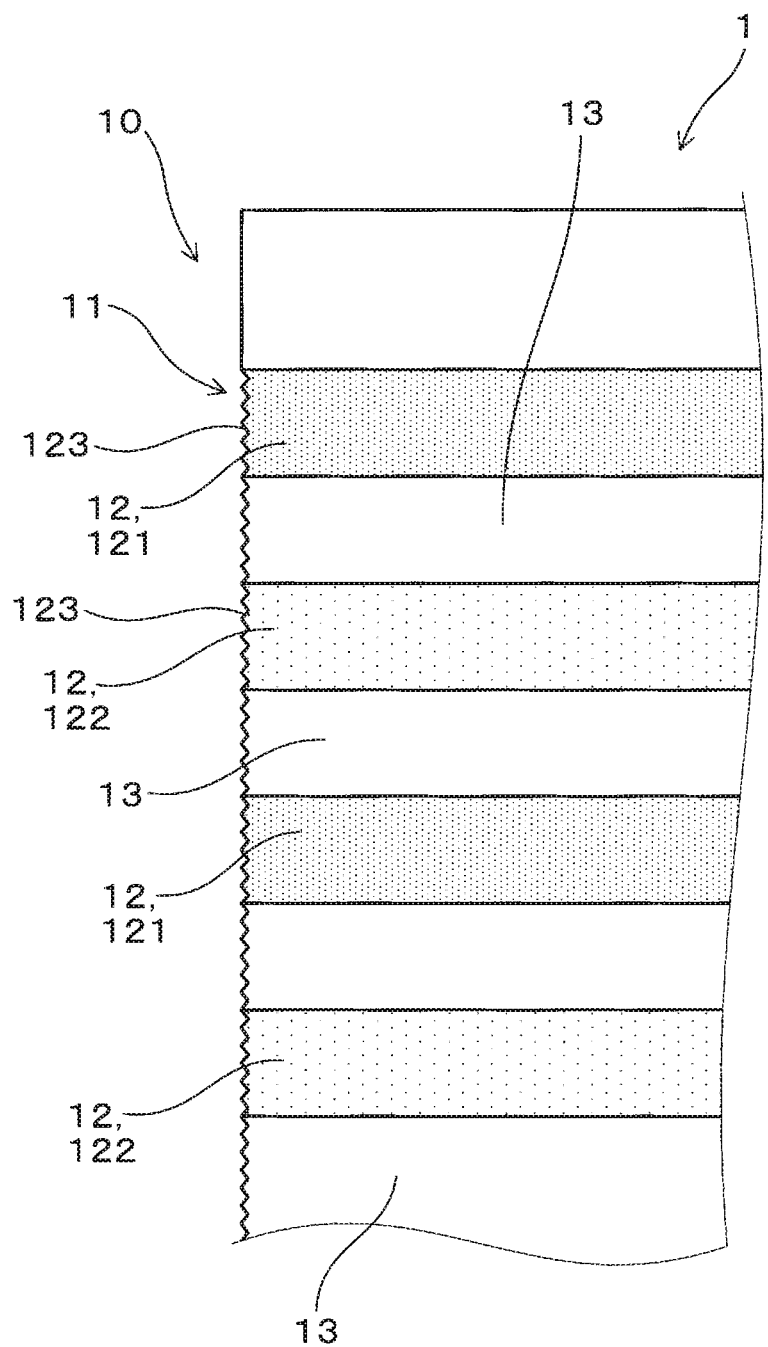

PARTICULATE MATTER DETECTION ELEMENT AND PARTICULATE MATTER DETECTION SENSOR

This application is the U.S. national phase of International Application No. PCT/JP2015/075432 filed 8 Sep. 2015, which designated the U.S. and claims priority to JP Patent Application No. 2014-226161 filed 6 Nov. 2014, the entire contents of each of which are hereby incorporated by reference.

TECHNICAL FIELD

The present invention relates to a particulate matter detection element and a particulate matter detection sensor.

BACKGROUND ART

An exhaust pipe of an internal combustion engine is provided with an exhaust gas purification apparatus for collecting particulate matter (Particulate Matter: PM) contained in exhaust gas. This exhaust gas purification apparatus is provided with a particulate matter detection apparatus including a particulate matter detection sensor for detecting an amount of particulate matter contained in the exhaust gas, and performs failure detection based on information obtained by this particulate matter detection apparatus.

Particulate matter detection sensors for use in an exhaust gas purification apparatus include one described in patent literature 1, for example. The particulate matter detection sensor of patent literature 1 includes a deposition part in which electrode layers and insulating layers are laminated alternately, with the end surfaces of the electrode layers being exposed. A plurality of detection electrodes arranged in parallel to one another are formed by the end surfaces of the electrode layers exposed in the deposition part.

CITATION LIST

Patent Literature

[PTL1]
 JP-A-2012-78130

SUMMARY OF THE INVENTION

Technical Problem

However, the particulate matter detection sensor of patent literature 1 involves the following problems. In the particulate matter detection sensor of patent literature 1, the electrode layers and the insulating layers are laminate alternately, and then the surface of the deposition part is polished smoothly so that the end surfaces of the electrode layers are exposed on the deposited part. In the deposition part smoothly polished as above, since the retentive force of deposited particulate matter is weak, the particulate matter deposited on the deposition part may easily detach due to the increase of the weight with the increase of the particulate matter or a change of the velocity of the exhaust gas. If the particulate matter deposited on the deposition part detaches, the output of the particulate matter detection sensor is lowered, and accordingly the detection accuracy is lowered.

The present invention has been made in view of such background to provide a particulate matter detection element and a particulate matter detection sensor that enable suppressing detaching of particulate matter and increasing the detection accuracy.

Solution to Problem

One aspect of the present invention is in a particulate matter detection element that includes a laminated part in which paired detection electrodes for detecting particulate matter contained in exhaust gas discharged from an internal combustion engine and insulating members having electrical insulation properties are laminated, at least part of the paired detection electrodes being exposed from the insulating members in a direction perpendicular to a lamination direction of the paired detection electrodes and the insulating members, to allow part of the particulate matter to deposit thereon, a surface roughness of at least the insulating member disposed between the paired detection electrodes being between 0.8 μm and 8.0 μm in 10-point average roughness.

Another aspect of the present invention is in a particulate matter detection sensor that includes the particulate matter detection element and a cylindrical cover member disposed so as to surround the periphery of the particulate matter detection element, the deposition part of the particulate matter detection element being disposed so as to face the distal end of the cover member in the axial direction of the cover member.

Advantageous Effects of the Invention

In the particulate matter detection element, the surface roughness of at least the insulating member is between 0.8 μm and 8.0 μm in 10-point average roughness so that minute unevenness is present on the surface of the insulating member. Since the particulate matter enters the minute unevenness, the retentive force of the particulate matter on the surface of the insulating member increases. Accordingly, it is possible to suppress loss of the particulate matter which deposits between the paired detection electrodes and forms a conduction path. This makes it possible to suppress lowering of the output of the particulate matter detection element and increase the detection accuracy.

In the particulate matter detection sensor, the particulate matter detection element that can suppress detaching of particulate matter as described above is used. Accordingly, even in a case where the deposition part is formed in the distal end of the particulate matter detection element which is susceptible to flow of exhaust gas, it is possible to suppress lowering of the output of the particulate matter detection sensor and to increase the detection accuracy.

The deposition part of the particulate matter detection element is disposed so as to face the distal end of the cover member. Accordingly even when the assembling angle of the particulate matter detection sensor is changed in the circumferential direction about the center axis of the particulate matter detection sensor, the direction of the deposition part relative to a flow direction of exhaust gas does not change. Therefore, since it is not necessary to manage the assembling angle of the particulate matter detection element in the circumferential direction, the particulate matter detection sensor can be assembled easily.

As described above, according to the present invention, it is possible to provide a particulate matter detection element and a particulate matter detection sensor that can suppress particulate matter from detaching and increase the detection accuracy.

BRIEF DESCRIPTION OF THE DRAWINGS

FIG. 7 is a partial enlarged view showing another example of the particulate matter detection element of embodiment 2 (corresponding to the perspective cross section along line II-II of FIG. 1).

DESCRIPTION OF EMBODIMENTS

Embodiment 1

An embodiment of a particulate matter detection element and a particulate matter detection sensor according to the present invention are explained with reference to FIGS. 1 to 4. FIG. 2 is drawn exaggerating the surface roughness of a deposition part which is different from its actual surface property (the same applying to later explained FIGS. 6 and 7).

Figure 1:
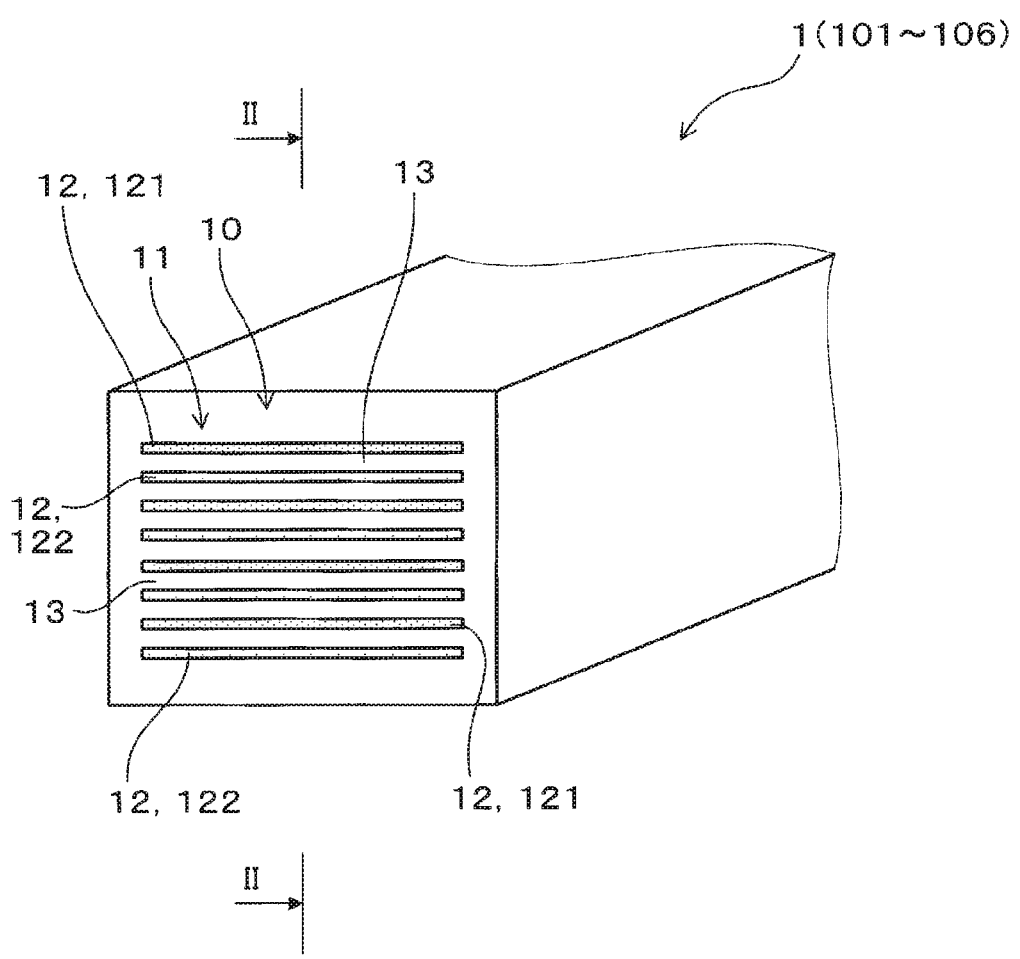
FIG. 1 is an explanatory view showing a particulate matter detection element of embodiment 1 according to the present invention.
Figure 2:
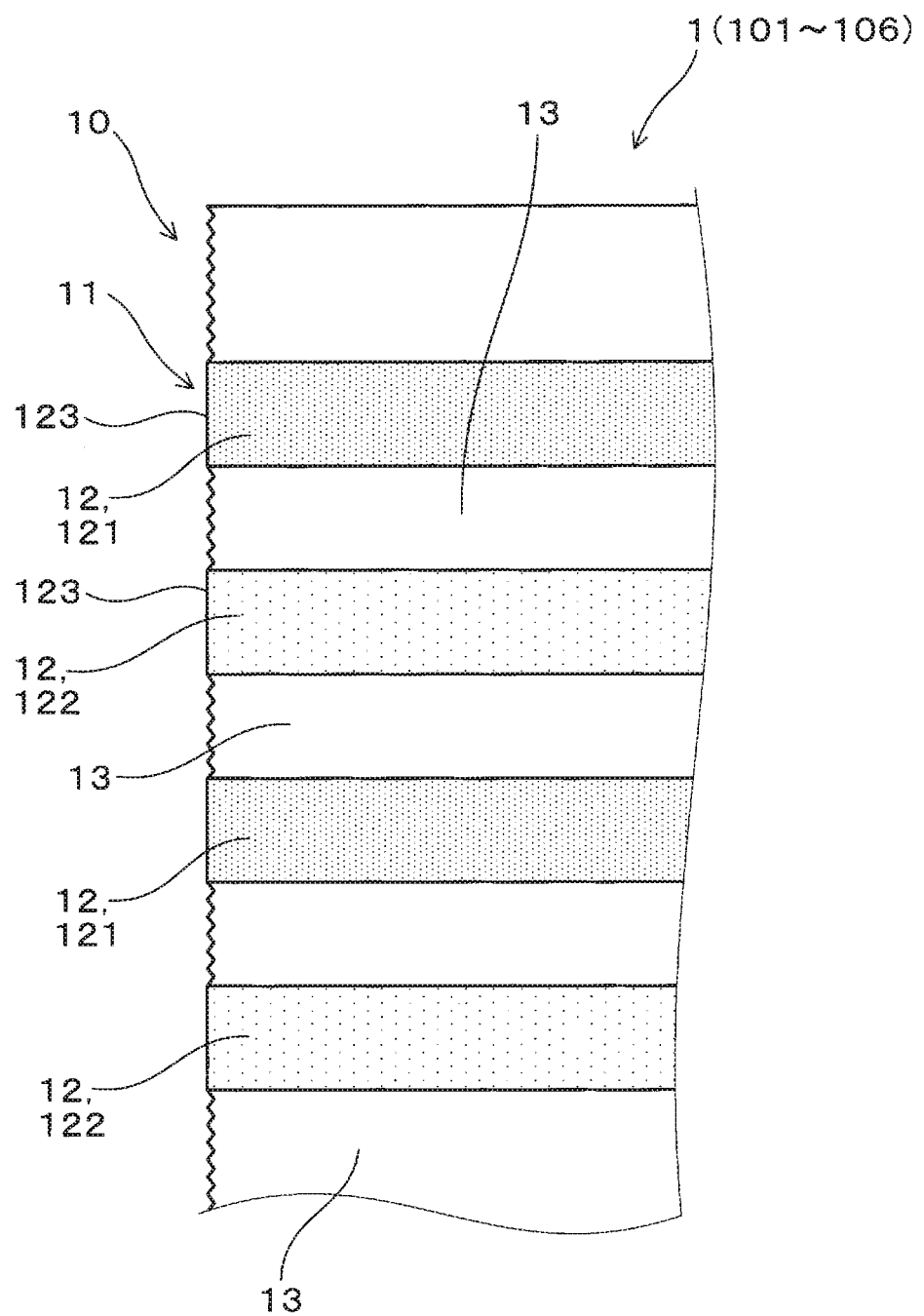
FIG. 2 is a partial enlarged view of a perspective cross section along line II-II of FIG. 1.

As shown in FIG. 1, a particulate matter detection element 1 includes a laminated part 11 in which paired detection electrodes 12 for detecting particulate matter contained in exhaust gas discharged from an internal combustion engine and insulating member 13 made of electrically insulating material are laminated.

The particulate matter detection element 1 includes a deposition part 10 in which at least part of the paired detection electrodes 12 is exposed in the direction perpendicular to the lamination direction of the paired detection electrodes 12 and the insulating members 13, and on which part of the particulate matter is deposited. The surface roughness of at least the insulating member 13 disposed between the paired detection electrodes 12 in the deposition part 10 is 2.0 µm in 10-point average roughness.

Figure 4:
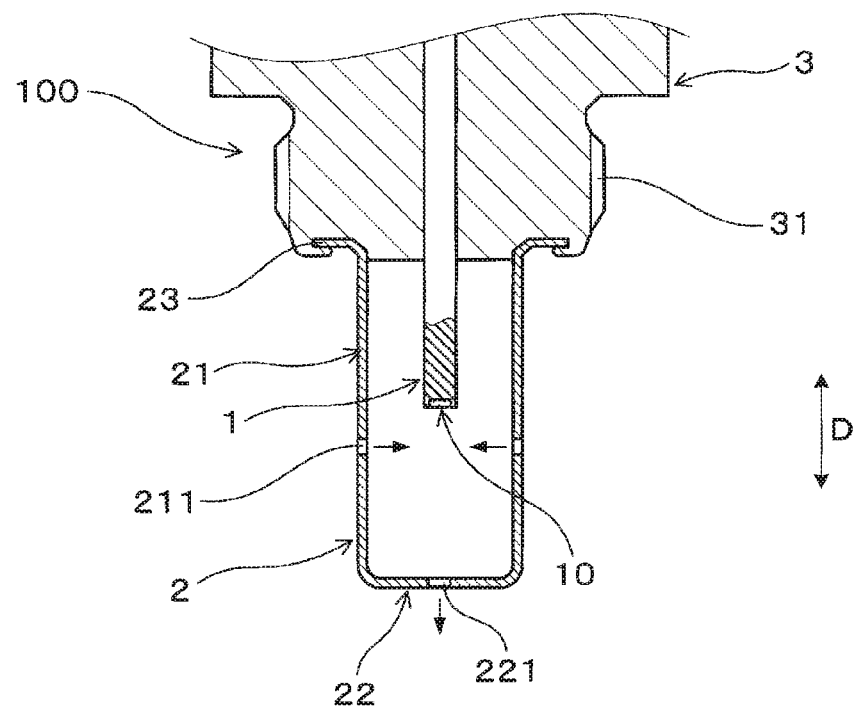
FIG. 4 is an explanatory view showing a particulate matter detection sensor of embodiment 1.

Further details are described in the following. As shown in FIG. 4, the particulate matter detection element 1 of this embodiment is one of components of a particulate matter detection sensor 100. The particulate matter detection sensor 100 is for detecting particulate matter contained in exhaust gas discharged from an internal combustion engine mounted on an automobile. Based on information obtained by the particulate matter detection sensor 100, failure detection of an exhaust gas purification apparatus is performed. The particulate matter detection sensor 100 is disposed so as to project to the inside of an exhaust pipe. The end side disposed inside the exhaust pipe in the axial direction D of the particulate matter detection sensor 100 is defined as the front end side, and the opposite side is defined as the proximal end side. In this embodiment, the axial direction D is the same as the vertical direction, the front end side being located downward, the proximal end side being located upward.

The particulate matter detection sensor 100 includes the above described particulate matter detection element 1, cover member 2 covering the periphery of the particulate matter detection element 1, and a housing member 3 holding these.

The housing member 3, which has a roughly cylindrical shape, holds the particulate matter detection element 1 inserted therein, and holds the cover member 2 at the distal end surface thereof. A male thread part 31 is formed in the outer peripheral side surface of the housing member 3. By screwing this male thread part 31 into a tapped hole formed penetrating through the exhaust pipe, the particulate matter detection sensor 100 can be fixed to the exhaust pipe with the distal end side of the particulate matter detection sensor 100 being exposed to the inside of the exhaust pipe. The particulate matter detection sensor 100 is installed downstream of the exhaust gas purification apparatus in the exhaust pipe.

The cover member 2 includes a cylindrical cover wall part 21 surrounding the particulate matter detection element 1, a cover bottom part 22 formed in the distal end of the cover wall part 21, and a brim part 23 standing from the proximal end of the cover wall part 21 toward the outer peripheral side. The cover member 2 is fixed to the housing member 3 by swaging the brim part 23 to the distal end surface of the housing member 3.

The cover wall part 21 is formed with exhaust gas introduction holes 211 penetrating therethrough. The exhaust gas introduction holes 211 have a circular shape, and are formed at even intervals along the circumferential direction of the cover wall part 21. The exhaust gas introduction holes 211 are formed at positions located more to the distal end side than the deposition part 10 of the particulate matter detection element 1 is. The number and positions of the exhaust gas introduction holes 211 can be set suitably.

The cover bottom part 22 is formed with an exhaust gas discharge hole 221 penetrating therethrough in the axial direction D at its center. This makes it possible to introduce the exhaust gas into the cover member 2 from the exhaust gas discharge hole 221, and form a flow of the exhaust gas to discharge the exhaust gas within the cover member 2 from the exhaust gas discharge hole 221.

Figure 3:
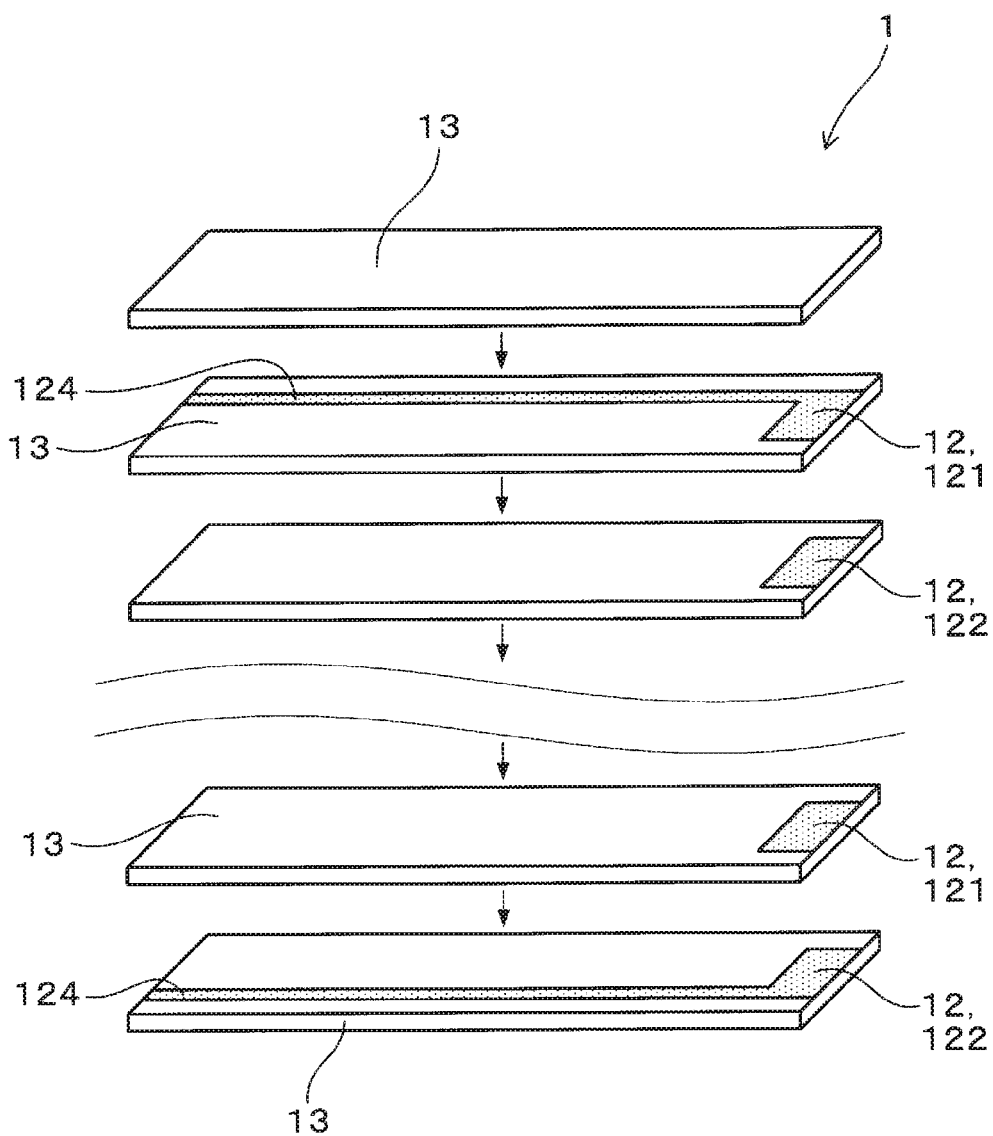
FIG. 3 is an explanatory view showing the structure of the particulate matter detection element embodiment 1.

As shown in FIGS. 1 to 3, the particulate matter detection element 1 includes the deposition part 10 on which particulate matter in the exhaust gas is deposited, and the detection electrodes 12 disposed apart from each other on the deposition part 10. The particulate matter detection element 1 is formed in a bar shape by laminating nine insulating members 13 made of plate-shaped ceramic material such as alumina, zirconia, magnesia or beryllia. Eight of the nine insulating members 13 are formed with the detection electrode 12 made of conductive material at the distal end side of the principal surface thereof, respectively. The detection electrode 12 is comprised of a positive electrode 121 and a negative electrode 122 which are disposed alternately when the insulating members 13 are laminated. The positive electrode 121 and the negative electrode 122, which are disposed at both ends in the lamination direction, are formed with a lead electrode part 124 that extends from the detection electrode 12, respectively.

The deposition part 10 is formed on the distal end side in the direction perpendicular to the lamination direction of the detection electrodes 12 and the insulating members 13 with the nine insulating members 13 being laminated. The deposition part 10 is formed with a laminated part 11 in which the insulating members 13 and the detection electrodes 12 are laminated alternately. The end surfaces of the detection electrodes 12 are exposed by being polished at their distal end parts after the insulating members 13 formed with the detection electrodes are laminated. The surface roughness of an exposed part 123 (the end surface) of the detection electrode 12 exposed in the deposition part 10 is smaller than or equal to 0.8 μm in 10-point average roughness. The surface roughness of the insulating member 13 disposed between the detection electrodes 12 in the deposition part 10 is 2.0 μm in 10-point average roughness. In this embodiment, the reference length of the 10-point average roughness is 200 μm. The reference length may comply with JIS B 0633. Regarding the surface roughness of the deposition part 10, the detection electrode 12 and the insulating member 13 may be different in surface roughness by suitable adjustment in view of hardness of the detection electrode 12 and the insulating member 12 and so on.

In the particulate matter detection element 1, the electric resistance value between the detection electrodes 12 decreases by conduction between the detection electrodes 12 exposed on the deposition part 10 due to particulate matter deposited on the deposition part 10. A voltage is applied between the detection electrodes 12, and accordingly the value of a current as an electrical signal flowing between the detection electrodes 12 is changed depending on a change of the electric resistance value between the detection electrodes 12. Therefore, the current outputted from the particulate matter detection element 1 is changed. That is, the current outputted from the particulate matter detection element 1 is changed depending on the deposition amount of the particulate matter on the deposition part 10, and accordingly has information regarding the deposition amount of the particulate matter. It is possible to detect the deposition amount of the particulate matter on the deposition part 10 by using this value of the current. In this embodiment, the current value detected by a particulate matter detection means is outputted to a control unit provided with a shunt resistor, and the control unit outputs a voltage calculated as the product of the current value and the shunt resistance. This voltage makes the output of the particulate matter detection sensor 100.

Next, the advantageous effects of this embodiment are explained.

In the particulate matter detection element 1, the surface roughness of the insulating member 13 is 2.0 μm in 10-point average roughness, so that minute unevenness is present on the surface of the insulating member 13. Since particulate matter enters the minute unevenness, the retentive force of the particulate matter on the surface of the insulating member 13 increases. Accordingly, it is possible to suppress detaching of the particulate matter which deposits between the paired detection electrodes 12 and forms a conduction path. This makes it possible to suppress a decrease of the output of the particulate matter detection element 1 and increase the detection accuracy.

The surface roughness of the insulating member 13 disposed between the paired detection electrodes 12 is between 2.0 μm and 4.5 μm in 10-point average roughness. Therefore, it is possible to obtain the particulate matter detection element 1 which is well balanced in detection sensitivity and detection accuracy, assuring productivity of the particulate matter detection element 1.

The surface roughness of the exposed part 123 exposed from the insulating member 13 of the detection electrodes 12 in the deposition part 10 is smaller than 0.8 μm in 10-point average roughness. Accordingly, the surface area of the detection electrode 12 can be made small so that particulate matter adhered to detection electrode 12 can be moved rapidly to the insulating member 13 disposed between the paired detection electrodes 12. Therefore, the detection sensitivity of the particulate matter detection element 1 can be increased.

In the particulate matter appearance sensor 100, the particulate matter detection element 1 capable of suppressing detaching of particulate matter is used as described above. Accordingly, even in the case where the deposition part 10 is formed in the distal end part of the particulate matter detection element 1 which is susceptible to flow of exhaust gas, it is possible to suppress a decrease of the output of the particulate matter detection sensor 100 to thereby increase the detection accuracy.

The deposition part 10 of the particulate matter detection element 1 is disposed so as to face the distal end of the cover member 2. Accordingly, even when the assembling angle of the particulate matter detection sensor 100 is changed in the circumferential direction about the center axis of the particulate matter detection sensor 100, the direction of the deposition part 10 relative to a flow direction of exhaust gas does not change. Therefore, since it is not necessary to manage the assembling angle of the particulate matter detection element 1, the particulate matter detection sensor 100 can be assembled easily.

As described above, according to the present invention, it is possible to provide the particulate matter detection element 1 and the particulate matter detection sensor 100 that can suppress detaching of particulate matter and increase the detection accuracy.

(Confirmation Test)

In this test, effects caused to the detection accuracy and detection sensitivity when the surface roughness of the insulating members 13 of the deposition part 10 of the particulate matter detection element 1 were confirmed.

In this test, comparisons in the detection accuracy and detection sensitivity were performed using the particulate matter detection element 1 described in the above embodiment 1 and the particulate matter detection element 1 in which the surface roughness of the insulating members 13 of the deposition part 10 was changed. The surface roughness of the insulating member 13 between the detection electrodes 12 of the deposition part 10 is 0.7 μm for particulate matter detection element 101, 0.8 μm for particulate matter detection element 102, 4.5 μm for the particulate matter detection element 103, 4.8 μm for particulate matter detection element 104, 8.0 μm for particulate matter detection element 105, and 8.2 μm for particulate matter detection element 106.

For the other structures, they are the same as embodiment 1. The reference signs used in this instance or drawings related to this instance, which are the same as the reference signs used in embodiment 1 denote the same constituent elements unless otherwise noted.

In an exhaust pipe in which the particulate matter detection element 1 is disposed, exhaust gas whose particulate matter concentration is 1 mg/m$^3$ was caused to flow at a discharge amount of 3420 L/min. The temperature of the exhaust gas in the vicinity of the particulate matter detection element 1 was 220 degrees C.

Figure 5:
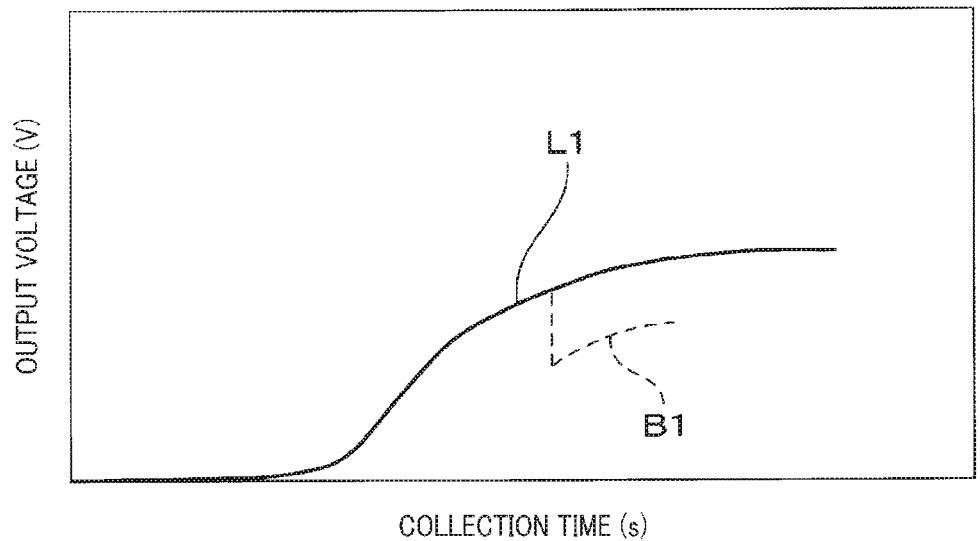
FIG. 5 is a graph showing an output decrease of the particulate matter detection element in a confirmation test.

Under these conditions, the detection accuracy and detection sensitivity of the particulate matter detection element 1 were confirmed. The detection accuracy was judged in accordance with presence or absence of a decrease of the output value due to detaching of particulate matter by monitoring the output (voltage) of the particulate matter detection element 1. FIG. 5 is a graph in which the vertical axis represents the output voltage (V) of the particulate matter detection element 1, and the horizontal axis represents the collection time (s). The output voltage of the particulate matter detection element 1 is null before a conduction path is formed between the paired detection electrodes 12. After a conduction path is formed between the paired detection electrodes 12, the output voltage increases with the increase of the deposition amount of particulate matter. When collected particulate matter deposits without detaching in the particulate matter detection element 1, the output voltage increases with the passage of time as shown by the solid line L. On the other hand, when there occurs detaching of the collected particulate matter, there occurs a sharp drop of the output voltage as shown by the broken line B1.

The detection sensitivity was judged in accordance with the dead mass in the particulate matter detection element 1. The dead mass is a mass of particulate matter contained in the exhaust gas that has flown through the exhaust pipe before a conduction path is formed in the particulate matter detection element 1 and the electric performance of the particulate matter detection element 1 is changed.

the detection electrodes 12 was set to 8.2 μm in 10-point average roughness. The dead mass was confirmed to be smaller than 30 mg when the surface roughness of the insulating member 13 between the detection electrodes 12 was set smaller than or equal to 4.5 μm in 10-point average roughness.

Hence, it is possible to obtain a particulate matter detection element 1 excellent in detection accuracy and detection sensitivity by setting the surface roughness of the insulating member 13 between the detection electrodes 12 between 0.8 μm and 8.0 μm in 10-point average roughness. It is possible to obtain a particulate matter detection element 1 further excellent in the detection sensitivity by setting the surface roughness of the insulating member 13 between the detection electrodes 12 smaller than or equal to 4.5 μm. In view of productivity of the particulate matter detection element 1, it is possible to increase the efficiency of polishing work to thereby increase the productivity of the particulate matter detection element 1 by setting it larger than or equal to 2.0 μm.

TABLE 1

| SURFACE ROUGHNESS | OUTPUT DECREASE | DETERMINATION 1 | DEAD MASS | DETERMINATION 2 | OVERALL DETERMINATION |
|---|---|---|---|---|---|
| 0.7 μm | PRESENT | X | 28 mg | ○ | X |
| 0.8 μm | ABSENT | ○ | 28 mg | ○ | ○ |
| 2.0 μm | ABSENT | ○ | 28 mg | ○ | ○ |
| 4.5 μm | ABSENT | ○ | 28 mg | ○ | ○ |
| 4.8 μm | ABSENT | ○ | 30 mg | ○ | ○ |
| 8.0 μm | ABSENT | ○ | 38 mg | ○ | ○ |
| 8.2 μm | ABSENT | ○ | 43 mg | X | X |

Table 1 shows the results of the confirmation test. In the column of OUTPUT DECREASE in Table 1, there is shown presence or absence of an output decreases of the particulate matter detection element 1. In the column of DETERMINATION 1, which shows the determination results of the output decrease of the particulate matter detection element 1, the symbol "x" was marked when there was an output decrease, and the symbol "○" was marked when there was no output decrease.

In the column of DEAD MASS, measured values of the dead mass are shown. In the column of DETERMINATION 1, which shows the determination results of the dead mass, the symbol "x" was marked when the dead mass was detected to be larger than 40 mg, and the symbol of "○" was marked when the dead mass was detected to be smaller than or equal to 40 mg. In the column of OVERALL DETERMINATION, the symbol of x was marked when at least one of the output decrease and dead mass corresponds to the symbol of "x" and the symbol of "○" was marked when both the output decrease and dead mass correspond to the symbol of "○".

As seen from Table 1, an output decrease was recognized when the surface roughness of the insulating member 13 between the detection electrodes 12 was set to 0.7 μm in 10-point average roughness. No output decrease was recognized when the surface roughness of the insulating member 13 between the detection electrodes 12 was set between 0.8 μm and 8.2 μm in 10-point average roughness.

The dead mass was measured to be smaller than or equal to 40 mg when the surface roughness of the insulating member 13 between the detection electrodes 12 was set between 0.7 μm and 8.0 μm in 10-point average roughness. The dead mass was measured to be larger than 40 mg when the surface roughness of the insulating member 13 between Embodiment 2

This embodiment is a modification of embodiment 1 in the structure of the particulate matter detection element 1. In the particulate matter detection element 1 shown in FIG. 6, the surface roughness of the surface of the detection electrodes 12 of the deposition part 10 is the same as the surface roughness of the surface of the insulating members 13.

In the particulate matter detection element 1 shown in FIG. 7, the surface roughness of the insulating members 13 other than the insulating member 13 disposed between the detection electrodes 12 on the deposition part 10 is made smooth. For the other structures, it is the same as embodiment 1. The reference signs used in this embodiment or drawings related to this embodiment, which are the same as the reference signs used in embodiment 1 denote the same constituent elements unless otherwise noted.

Figure 6:
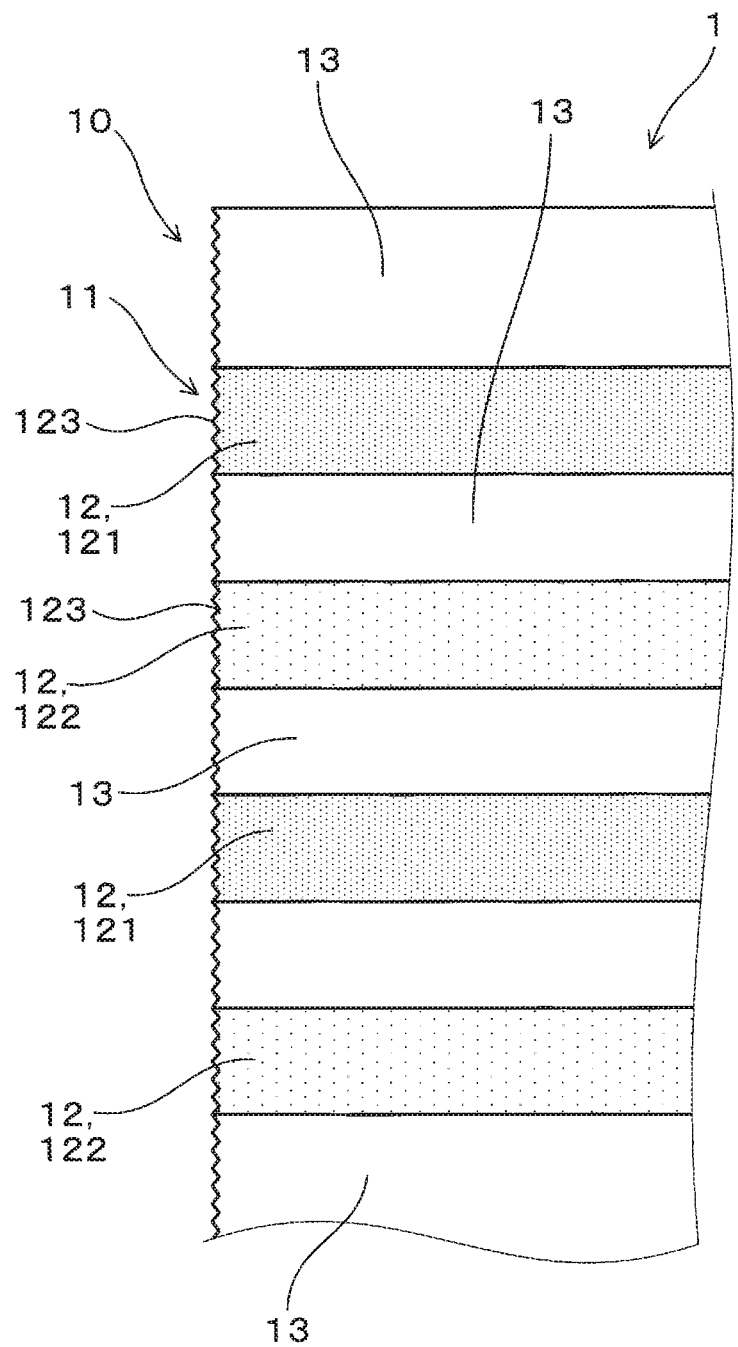
FIG. 6 is a partial enlarged view showing an example of a particulate matter detection element of embodiment 2 (corresponding to the perspective cross section along line II-II of FIG. 1).

In the particulate matter detection element 1 shown in FIG. 6, since the front surface of the deposition part 10 is uniform in surface roughness, the workability during polishing can be increased to thereby increase the productivity. In the particulate matter detection element 1 shown in FIG. 7, since the area to be polished of the deposition part 10 is small, the working time for polishing can be shortened to thereby increase the productivity. Also according to this embodiment, the same advantageous effects as those of embodiment 1 can be obtained.

REFERENCE SIGNS LIST 1 particulate matter detection element
10 deposition part
11 laminated part 12 detection electrode
13 insulating member

The invention claimed is:

1. A particulate matter detection element including a laminated part in which paired detection electrodes for detecting particulate matter contained in exhaust gas discharged from an internal combustion engine and insulating members made of electrically insulating material are laminated alternately, the particulate matter detection element comprising:
   a deposition part in which at least part of the paired detection electrodes is exposed from the insulating members in a direction perpendicular to a lamination direction of the paired detection electrodes and the insulating members, a part of the particulate matter being caused to deposit on the deposition part, wherein
   a surface roughness of at least the insulating member disposed between the paired detection electrodes in the deposition part is between 0.8 µm and 8.0 µm when calculated using a 10-point average.

2. The particulate matter detection element according to claim 1, wherein the surface roughness of the insulating member disposed between the paired detection electrodes is between 2.8 µm and 4.5 µm when calculated using a 10-point average.

3. The particulate matter detection element according to claim 1, wherein a surface roughness of an exposed part of the deposition part, which is exposed from the insulating members of the detection electrodes is smaller than 0.8 µm when calculated using a 10-point average.

4. A particulate matter detection sensor comprising:
   the particulate matter detection element recited in claim 1; and
   a cylindrical cover member disposed so as to surround a periphery of the particulate matter detection element,
   wherein the deposition part of the particulate matter detection element is disposed so as to face a distal end of the cover member in an axial direction of the cover member.

\* \* \* \* \*